United States Patent
Matveeva et al.

(10) Patent No.: US 12,349,684 B2
(45) Date of Patent: Jul. 8, 2025

(54) METHOD OF DOUGH RELAXATION INVOLVING ENDOPEPTIDASES

(71) Applicant: Novozymes A/S, Bagsvaerd (DK)

(72) Inventors: Irina Victorovna Matveeva, Moscow (RU); Katja Puder, Soeborg (DK); Sajid Akbar, Kerala (IN)

(73) Assignee: Novozymes A/S, Bagsvaerd (DK)

( * ) Notice: Subject to any disclaimer, the term of this patent is extended or adjusted under 35 U.S.C. 154(b) by 635 days.

(21) Appl. No.: 17/625,205

(22) PCT Filed: Aug. 5, 2020

(86) PCT No.: PCT/EP2020/071984
§ 371 (c)(1),
(2) Date: Jan. 6, 2022

(87) PCT Pub. No.: WO2021/023767
PCT Pub. Date: Feb. 11, 2021

(65) Prior Publication Data
US 2022/0240521 A1   Aug. 4, 2022

(30) Foreign Application Priority Data

Aug. 7, 2019   (IN) .............................. 201941031941

(51) Int. Cl.
*A21D 8/04* (2006.01)
*C12N 9/50* (2006.01)

(52) U.S. Cl.
CPC .............. *A21D 8/042* (2013.01); *C12N 9/50* (2013.01); *C12Y 304/21004* (2013.01)

(58) Field of Classification Search
CPC ........ A21D 8/042; A21D 13/066; A21D 2/26; A21D 8/04; A21D 10/002; C12N 9/50; C12Y 304/21
USPC .............. 435/68.1; 426/20, 549, 52
See application file for complete search history.

(56) References Cited

U.S. PATENT DOCUMENTS

| | | | |
|---|---|---|---|
| 2011/0097448 A1 | 4/2011 | Wong et al. | |
| 2016/0237466 A1 | 8/2016 | Landowski et al. | |

FOREIGN PATENT DOCUMENTS

| | | |
|---|---|---|
| CN | 104427878 A | 3/2015 |
| CN | 107927058 A | 4/2016 |
| CN | 1961686 A | 5/2017 |
| CN | 109475130 A | 3/2019 |
| EP | 2595488 B1 | 12/2019 |
| WO | 2009/147103 A2 | 12/2009 |
| WO | 2009/155557 A2 | 12/2009 |
| WO | 2012010592 A1 | 1/2012 |
| WO | 2013/092731 A1 | 6/2013 |
| WO | 2014006090 A1 | 1/2014 |
| WO | 2015/004241 A2 | 1/2015 |
| WO | 2018010966 A1 | 1/2018 |

OTHER PUBLICATIONS

Ahmed et al., American Journal of Food Science and Nutrition Research, vol. 2, No. 2, pp. 62-66 (2015).
Anonymous, Sigma Prod. No. p. 5380 (2016).
Gaines et al., Cereal Chemistry, vol. 66, No. 2, pp. 73-78 (1989).
Hassan et al., American Journal of Food Science and Nutrition Research, vol. 1, No. 1, pp. 1-7 (2013).
Kweon et al., Cereal Chemistry, vol. 87, No. 5, pp. 415-419 (2010).
Pedersen et al., Journal of Food Science, vol. 70, No. 2, pp. E152-E158 (2005).
Yao et al., Food & Machinery, vol. 34, No. 3, pp. 39-43 (2018).
Li et al., 2000, Beijing China Light Industry Press, 73-78—Tr.

*Primary Examiner* — Hong T Yoo
(74) *Attorney, Agent, or Firm* — Yoshimi D. Barron

(57) ABSTRACT

A method for increasing the softness and the relaxation of a dough comprising a) adding at least one endopeptidase having at least 60% identity to SEQ ID NO:1 or SEQ ID NO:2 to flour or to a dough comprising a flour, wherein no L-cystein and/or sodium metabisulfite is added to the dough; b) kneading the dough; and c) making the dough into an edible product.

13 Claims, No Drawings

Specification includes a Sequence Listing.

METHOD OF DOUGH RELAXATION INVOLVING ENDOPEPTIDASES

CROSS-REFERENCE TO RELATED APPLICATIONS

This application is a 35 U.S.C. 371 national application of international application no. PCT/EP2020/071984 filed Aug. 5, 2020, which claims priority or the benefit under 35 U.S.C. 119 of Indian Application No. 201941031941 filed Aug. 7, 2019. The content of each application is fully incorporated herein by reference.

REFERENCE TO A SEQUENCE LISTING

This application contains a Sequence Listing in computer readable form, which is incorporated herein by reference.

FIELD OF THE INVENTION

The present invention relates to a process for improving dough rheology, such as improving the relaxation and the softness of the dough, when producing, e.g., bread, flat bread, crackers, pizzas, pasta, noodles, laminated baking products, biscuits, baguettes, and hamburgers.

BACKGROUND OF THE INVENTION

Today, in the industrial dough-making processes, it is known to add dough-improving additives to dough in order to improve parameters such as texture, volume, extensibility, pan flow, and machine ability of the dough.

L-cysteine and sodium metabisulfite (SMS) are known dough-improving additives, used to improve the rheological properties of the dough, such as softness, extensibility, extent of relaxation, etc.

There is a need for finding biological solutions for improving the rheology of the dough such as improving relaxation, extensibility, and softness in the dough production, when making products such as bread, flat bread, crackers, pizzas, pasta, noodles, laminated baking products, biscuits, baguettes, and hamburgers.

SUMMARY OF THE INVENTION

Surprisingly, the inventors have found that a special type of an endopeptidase improves the relaxation of a dough, whereby addition of compounds like L-Cysteine and/or sodium metabisulfite (SMS) may be avoided, so we claim:

A method for increasing the softness and relaxation of a dough comprising
  a) adding at least one endopeptidase having at least 60% identity to SEQ ID NO:1 or SEQ ID NO:2 to flour or to a dough comprising a flour, wherein no L-cystein and/or sodium metabisulfite is added to the dough;
  b) kneading the dough; and
  c) making the dough into an edible product.

In one embodiment, the edible product is selected from the group consisting of bread, flat bread, crackers, pasta, noodles, laminated baking products, biscuits, baguettes, hamburgers, and pizzas.

In one embodiment, the dough is made into biscuits.

In one embodiment, the flour is selected from the group consisting of wheat flour, corn flour, rye flour, barley flour, oat flour, rice flour, sorghum flour, and a combination thereof.

In one embodiment, the amount of energy for kneading the dough is reduced compared to a method wherein no endopeptidase having at least 60% identity to SEQ ID NO:1 or SEQ ID NO:2 is added to the dough.

In one embodiment, the endopeptidase is added in an amount in the range of 0.1-1000 mg of enzyme protein per kg of flour.

In one embodiment, the shape of the edible product is better maintained compared to a method wherein no endopeptidase having at least 60% identity to SEQ ID NO:1 or SEQ ID NO:2 is added to the dough.

In one embodiment, the dough has an extensibility which is better than the extensibility of a dough which is prepared under the same conditions, but without treatment with the endopeptidase.

In one embodiment, the eating quality of the edible product is better than the eating quality of an edible product which is prepared under the same conditions, but without treatment with the endopeptidase.

In one embodiment, the dough further comprises one or more enzymes selected from the group consisting of amylase, maltogenic amylase, beta amylase, aminopeptidase, carboxypeptidase, catalase, cellulytic enzyme, chitinase, cutinase, cyclodextrin glycosyltransferase, deoxyribonuclease, esterase, glucan 1,4-alpha-maltotetrahydrolase, glucanase, galactanase, alpha-galactosidase, beta-galactosidase, glucoamylase, glucose oxidase, alpha-glucosidase, beta-glucosidase, haloperoxidase, hemicellulytic enzyme, invertase, laccase, lipase, mannanase, mannosidase, oxidase, pectinolytic enzymes, peroxidase, phospholipase, phytase, polyphenoloxidase, proteolytic enzyme, ribonuclease, transglutaminase, and xylanase.

In one embodiment, we claim a premix comprising an endopeptidase having at least 60% identity to SEQ ID NO:1 or SEQ ID NO:2 and flour.

In one embodiment, the premix further comprises one or more enzymes selected from the group consisting of amylase, maltogenic amylase, beta amylase, aminopeptidase, carboxypeptidase, catalase, cellulytic enzyme, chitinase, cutinase, cyclodextrin glycosyltransferase, deoxyribonuclease, esterase, glucan 1,4-alpha-maltotetrahydrolase, glucanase, galactanase, alpha-galactosidase, beta-galactosidase, glucoamylase, glucose oxidase, alpha-glucosidase, beta-glucosidase, haloperoxidase, hemicellulytic enzyme, invertase, laccase, lipase, mannanase, mannosidase, oxidase, pectinolytic enzymes, peroxidase, phospholipase, phytase, polyphenoloxidase, proteolytic enzyme, ribonuclease, transglutaminase, and xylanase.

In one embodiment, we claim the use se of an endopeptidase having at least 60% identity to SEQ ID NO:1 or SEQ ID NO:2 for increasing the extensibility of a dough, wherein no L-cystein and/or sodium metabisulfite is added to the dough.

In one embodiment, we claim the use of an endopeptidase having at least 60% identity to SEQ ID NO:1 or SEQ ID NO:2 for improving the eating quality of an edible product, wherein no L-cystein and/or sodium metabisulfite is added to the edible product.

DETAILED DESCRIPTION OF THE INVENTION

Definitions

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labelled "longest identity" (obtained using the—no brief option) is used as the percent identity and is calculated as follows:

(Identical Residues×100)/(Length of Alignment−Total Number of Gaps in Alignment)

Variant: The term "variant" means a polypeptide having endopeptidase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding one or more amino acids adjacent to and immediately following the amino acid occupying a position.

Improved property: When the endopeptidase according to the invention is incorporated into a flour and/or a dough in effective amounts, one or more properties are improved compared to a flour and/or a dough in which the enzyme is not added.

The improved property may be determined by comparison of a dough and/or a baked product prepared with and without addition of the enzyme of the present invention in accordance with the methods described below.

Organoleptic qualities may be evaluated using procedures well established in the baking industry, and may include, for example, the use of a panel of trained taste-testers.

Improved extensibility: The term "improved extensibility of the dough" is defined herein as the property of dough that can be subjected to increased stretching without rupture.

The increased stretching is a very important parameter as it means that it is possible to, e.g., obtain very thin doughs.

Increased relaxation: The term "increased relaxation" is defined herein as the property that the endopeptidase according to the invention may be able to substitute chemical relaxation agents used to optimize dough rheology and ensure final products with improved quality, smooth surfaces and round edges.

Increased softness: The term "increased softness of the dough" is defined herein as the property of a dough that is softer than a control dough wherein no endopeptidase according to the invention has been added—as evaluated by the skilled baker.

Increased elasticity: The term "increased elasticity of the dough" is defined herein as the property of dough which has a higher tendency to regain its original shape after being subjected to a certain physical strain.

Increased stability of the dough: The term "increased stability of the dough" is defined herein as the property of dough that is less susceptible to mechanical abuse thus better maintaining its shape and volume and is evaluated by the ratio of height:width of a cross section of a loaf after normal and/or extended proof.

Improved machine ability: The term "improved machine ability of the dough" is defined herein as the property of a dough that is generally less sticky and/or firmer and/or more elastic.

Increased volume of the dough/the baked product: The term "increased volume of the dough/baked product" is measured as the volume of a dough or the volume of a given loaf of bread. The volume may, e.g., be determined by the rape seed displacement method, or by a skilled baker, or by using a Volscan profiler 600.

Improved crumb structure of the baked product: The term "improved crumb structure of the baked product" is defined herein as the property of a baked product regarding crumb uniformity, cell wall thickness, and the size of the individual gas cells pores on the slice of bread.

The crumb structure of the baked product is usually evaluated visually by the baker or by digital image analysis as known in the art (e.g., C-cell, Calibre Control International Ltd, Appleton, Warrington, UK).

Improved softness of the baked product: The term "improved softness of the baked product" is the opposite of "firmness" and is defined herein as the property of a baked product that is more easily compressed and is evaluated either empirically by the skilled test baker or measured by use of a texture analyser (e.g., TAXT2 or TA-XT Plus from Stable Micro Systems Ltd, surrey, UK) as known in the art.

Dough Compositions

The present invention may solve the problem caused by flour quality inconsistency, because overly strong flour results in dough that does not flow properly in the pans, resulting in misshapen loaves, buns, pizza, etc.

The present invention may help to secure the yeast dough relaxation for baked goods such as hamburger buns, yeast baked goods, pizza, pan bread, etc., allowing to proceed with various flour quality, improving the dough rheological properties, dough extensibility, the pan flow of dough, resulting in appealing appearance of baked goods, better volume, and higher quality of pan bread.

The invention may solve the problem of flour quality for biscuits production, helping to weaken the gluten, increase dough extensibility, reduce energy for kneading, maintain the shape of laminated dough biscuits, secure the size and shapes of biscuits, improve mouthfeel, appearance, etc.

As used herein "dough" means any dough used to prepare a baked or cooked product.

According to the present invention, the dough used to prepare a baked or cooked product may be made from any suitable dough ingredients comprising flour. The flour used to prepare the dough according to the invention may be any suitable flour source, e.g., flour sourced from grains, such as, wheat flour, corn flour, rye flour, barley flour, oat flour, rice flour, sorghum flour, potato flour, soy flour, flour from pulses, and combinations thereof.

As used herein, a "flattened dough" means a dough, which typically has a thickness of one millimeter to a few centimeters.

According to the invention, the dough may be used for making for any baked or cooked products, e.g., biscuits, crackers, pizzas, flat bread, bread, especially pan bread, buns, especially hamburger buns, baguettes, pasta, and noodles.

The dough according to the invention is especially useful to make biscuits.

According to the present invention, a biscuit may be defined as hard dough or short dough:

Hard dough: This dough is similar to bread dough, with a stiff consistency. It is a lean dough as the fat and sugar content are low relative to the flour content. Semisweet, unsweetened, and savory biscuits are made from hard dough.

Short dough: This dough is more closely related to cake dough, although with much less water. The name refers to their high levels of shortening or fat in relation to flour content. This fat reduces the extensibility of the dough meaning these biscuits are more likely to break. The dough also has a high sugar content.

The biscuit according to the invention may be any biscuit known in the art.

One example of a hard dough biscuit is a cracker. A cracker is a baked food product made from a sheeted dough, and typically not sweet. Flavorings or seasonings, such as salt, herbs, seeds, and/or cheese, may be added to the dough or sprinkled on top before baking as known in the art. Crackers come in many shapes and sizes—round, square, triangular, etc. If a leavening agent is used, sodium acid pyrophosphate (SAPP) and/or sodium bi-carbonate and/or ammonium bi-carbonate may be used.

A flat bread may be made from a simple mixture of flour, water, and salt and then thoroughly rolled into flattened dough. Flat bread has a very quick baking time (often <2 minutes).

The flat bread may be unleavened, i.e., made without a yeast, or leavened, e.g., made with a yeast. The flat bread may include further optional ingredients, such as olive oil, sesame oil, shortenings, and spices. Examples of flat bread include tortilla, pita, Arabic bread, and Indian flat bread, including wheat and gluten free flat bread.

Further non-limiting examples of flat bread include lavash, baladi, barbari, sangak, tandoor, taftoon, shami, halabi, mafrood, burr, bairuti, pocket bread, naan, phulka, chapatti, paratha, Arabic pita, Lebanese, mafrood, hapati, sangak, roti, taboon, shrak, mashrouh, nasir, tannoor, lavash, and taftan.

The dough according to the invention may also be used to make pizzas. Pizza is a yeasted flatbread typically topped with, e.g., tomato sauce and cheese, and baked in an oven.

The flattened dough according to the invention may also be used to make noodles and pasta. Noodles are made from unleavened dough which is stretched, extruded, or rolled flat and cut into one of a variety of shapes. Noodles are usually cooked in boiling water, sometimes with cooking oil and/or salt added. They may be pan-fried or deep-fried. Pasta is typically a noodle made from an unleavened dough of a durum wheat flour mixed with water and/or eggs and formed into sheets or various shapes, then cooked by boiling. Pasta can also be made with flour from other cereals or grains.

The dough according to the invention may also be used to make laminated baking products.

A laminated dough is a culinary preparation consisting of many thin layers of dough separated by butter, produced by repeated folding and rolling. Such doughs may contain many layers, i.e., more than 10 layers. During baking, the water in the butter vaporizes and expands, causing the dough to puff up and separate, while the lipids in the butter essentially fry the dough, resulting in a light, flaky product. Examples of laminated doughs include Croissant pastry, and other pastries such as Danish pastry, Flaky pastry, and Puff pastry.

Normally, it should not be needed, but the dough according to the present invention may also comprise other conventional dough relaxation ingredients such as deactivated yeast, glutathione, malt, sorbic acid, and/or yeast extract.

The dough according to the invention may also comprise one or more emulsifiers. Emulsifiers also serve to improve dough extensibility. Examples of suitable emulsifiers are mono- or diglycerides, polyoxyethylene stearates, diacetyl tartaric acid esters of monoglycerides, sugar esters of fatty acids, propylene glycol esters of fatty acids, polyglycerol esters of fatty acids, lactic acid esters of monoglycerides, acetic acid esters of monoglycerides, lecithin or phospholipids, or ethoxylated monoglycerides. Particular emulsifiers include monoglycerides, diacetyl tartaric acid esters of monoglyceride (DATEM) and sodium stearoyl lactylate (SSL).

Other conventional ingredients that may be added to the dough include proteins, such as milk powder, gluten, and soy; eggs (either whole eggs, egg yolks or egg whites); an oxidant such as ascorbic acid, potassium bromate, potassium iodate, azodicarbonamide (ADA), ammonium persulfate or potassium persulfate; a sugar such as sucrose, dextrose, glucose, etc.; a salt such as sodium chloride, calcium acetate, sodium sulfate or calcium sulfate, diluents such silica dioxide, starch of different origins. Still other convention ingredients include hydrocolloids such as CMC, guar gum, xanthan gum, locust bean gum, etc. Modified starches may be also used.

The dough according to the present invention may be a fiber dough, e.g., the dough may contain grains, e.g., whole wheat, and/or are enriched with extra fibres in the form of, e.g., cereal bran, e.g., wheat bran. Wheat bran is produced as a side product of milling wheat into white flour.

Normally, fibres are divided into fine fibres, medium fibres, and coarse fibres as known in the art. Fine fibres are particularly useful in the present invention.

In addition to preparing fresh dough or fresh dough products, the present invention is also directed to a method for preparing a frozen dough or a frozen dough product.

The present invention is particularly useful for preparing flattened dough and products obtained from flattened dough in industrialized processes, where the products are prepared mechanically using automated or semi-automated equipment.

Enzymes

Endopeptidase According to the Invention

The term endopeptidase as used herein is an enzyme that hydrolyses internal peptide bonds (has endopeptidase activity).

There are no limitations on the origin of the endopeptidase for use according to the invention. Thus, the term endopeptidase includes not only natural or wild-type endopeptidases, but also any mutants, variants, fragments etc. thereof exhibiting endopeptidase activity, as well as synthetic endopeptidases, such as shuffled endopeptidases.

Genetically engineered endopeptidase variants can be prepared as is known in the art. Examples of endopeptidase variants are endopeptidases in which one or more amino acids have been deleted, inserted, or substituted with other amino acids.

According to the present invention, the endopeptidase has at least 60% identity to SEQ ID NO:1 or SEQ ID NO:2, e.g., at least 61% identity to SEQ ID NO:1 or SEQ ID NO:2, e.g., at least 62% identity to SEQ ID NO:1 or SEQ ID NO:2, e.g., at least 63% identity to SEQ ID NO:1 or SEQ ID NO:2, e.g., at least 64% identity to SEQ ID NO:1 or SEQ ID NO:2, e.g., at least 65% identity to SEQ ID NO:1 or SEQ ID NO:2, e.g., at least 66% identity to SEQ ID NO:1 or SEQ ID NO:2, e.g., at least 67% identity to SEQ ID NO:1 or SEQ ID NO:2, e.g., at least 68% identity to SEQ ID NO:1 or SEQ ID NO:2, e.g., at least 69% identity to SEQ ID NO:1 or SEQ ID NO:2, e.g., at least 70% identity to SEQ ID NO:1 or SEQ ID NO:2, e.g., at least 71% identity to SEQ ID NO:1 or SEQ ID NO:2, e.g., at least 72% identity to SEQ ID NO:1 or SEQ ID NO:2, e.g., at least 73% identity to SEQ ID NO:1 or SEQ ID NO:2, e.g., at least 74% identity to SEQ ID NO:1 or SEQ ID NO:2, e.g., at least 75% identity to SEQ ID NO:1 or SEQ ID NO:2, e.g., at least 76% identity to SEQ ID NO:1 or SEQ ID NO:2, e.g., at least 77% identity to SEQ ID NO:1 or SEQ ID NO:2, e.g., at least 78% identity to SEQ ID NO:1 or SEQ ID NO:2, e.g., at least 79% identity to SEQ ID NO:1 or SEQ ID NO:2, e.g., at least 80% identity to SEQ ID NO:1 or SEQ ID NO:2, e.g., e.g., at least 81% identity to SEQ ID NO:1 or SEQ ID NO:2, e.g., at least 82% identity to SEQ ID NO:1 or SEQ ID NO:2, e.g., at least 83% identity to SEQ ID NO:1 or SEQ ID NO:2, e.g., at least 84% identity to SEQ ID NO:1 or SEQ ID NO:2, e.g., at least 85% identity to SEQ ID NO:1 or SEQ ID NO:2, e.g., at least 86% identity to SEQ ID NO:1 or SEQ ID NO:2, e.g., at least 87% identity to SEQ ID NO:1 or SEQ ID NO:2, e.g., at least 88% identity to SEQ ID NO:1 or SEQ ID NO:2, e.g., at least 89% identity to SEQ ID NO:1 or SEQ ID NO:2, e.g., at least 90% identity to SEQ ID NO:1 or SEQ ID NO:2, e.g., e.g., at least 91% identity to SEQ ID NO:1 or SEQ ID NO:2, e.g., at least 92% identity to SEQ ID NO:1 or SEQ ID NO:2, e.g., at least 93% identity to SEQ ID NO:1 or SEQ ID NO:2, e.g., at least 94% identity to SEQ ID NO:1 or SEQ ID NO:2, e.g., at least 95% identity to SEQ ID NO:1 or SEQ ID NO:2, e.g., at least 96% identity to SEQ ID NO:1 or SEQ ID NO:2, e.g., at least 97% identity to SEQ ID NO:1 or SEQ ID NO:2, e.g., at least 98% identity to SEQ ID NO:1 or SEQ ID NO:2, e.g., at least 99% identity to SEQ ID NO:1 or SEQ ID NO:2.

In one embodiment, the endopeptidase is SEQ ID NO:1 or SEQ ID NO:2.

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labelled "longest identity" (obtained using the—nobrief option) is used as the percent identity and is calculated as follows:

(Identical Residues×100)/(Length of Alignment−
Total Number of Gaps in Alignment)

An endopeptidase for use according to the invention may be a microbial endopeptidase, preferably a bacterial endopeptidase, the term bacterial indicating that the endopeptidase is derived from, or originates from, a bacterium, or is an analogue, a fragment, a variant, a mutant, or a synthetic endopeptidase derived from a bacterium. It may be produced or expressed in the original wild-type bacterial strain, in another microbial strain, or in a plant; i.e., the term covers the expression of wild-type, naturally occurring endopeptidases, as well as expression in any host of recombinant, genetically engineered or synthetic endopeptidases.

Examples of bacterial endopeptidases applicable for use according to the invention are endopeptidases from *Nocardiopsis*, in particular *Nocardiopsis alba* (previously *Nocardiopsis dassonvillei*) NRRL 18133 disclosed in WO 88/03947.

In the process of the invention, the endopeptidase may be purified. The term "purified" as used herein covers enzyme protein preparations where the preparation has been enriched for the enzyme protein in question. Such enrichment could for instance be the removal of the cells of the organism from which an extracellular enzyme protein was produced, the removal of non-protein material by a protein specific precipitation or the use of a chromatographic procedure where the enzyme protein in question is selectively adsorbed and eluted from a chromatographic matrix. The endopeptidase may have been purified to an extent so only minor amounts of other proteins are present. The expression "other proteins" relate in particular to other enzymes. An endopeptidase to be used in the method of the invention may be "substantially pure", i.e., substantially free from other components from the organism in which it was produced, which may either be a naturally occurring microorganism or a genetically modified host microorganism for recombinant production of the endopeptidase.

An endopeptidase according to the invention may typically be added in an effective amount such as in the range of 0.1-1000 mg of enzyme protein per kg of flour, e.g., 1-500 mg of enzyme protein per kg of flour, e.g., 1-200 mg of enzyme protein per kg of flour.

Additional Enzymes

Optionally, one or more additional enzymes, such as amylase, maltogenic amylase, beta amylase, catalase, cellulytic enzyme, chitinase, cutinase, cyclodextrin glycosyltransferase, deoxyribonuclease, esterase, glucan 1,4-alpha-maltotetrahydrolase, glucanase, galactanase, alpha-galactosidase, beta-galactosidase, glucoamylase, glucose oxidase, alpha-glucosidase, beta-glucosidase, haloperoxidase, hemicellulytic enzyme, invertase, laccase, lipase, mannanase, mannosidase, oxidase, pectinolytic enzymes, peroxidase, phospholipase, phytase, polyphenoloxidase, proteolytic enzyme, ribonuclease, transglutaminase, and xylanase may be used together with the enzyme composition according to the invention.

The additional enzyme(s) may be of any origin, including mammalian, plant, and microbial (bacterial, yeast or fungal) origin.

Suitable commercial alpha-amylase compositions include, e.g., BAKEZYME P 300 (available from DSM) and FUNGAMYL 4000 BG, FUNGAMYL 800 L, FUNGAMYL ULTRA BG, and FUNGAMYL ULTRA SG (available from Novozymes A/S).

The maltogenic alpha-amylase (EC 3.2.1.133) may be from *Bacillus*. A maltogenic alpha-amylase from *B. stearothermophilus* strain NCIB 11837 is commercially available from Novozymes A/S under the tradename Novamyl®.

The maltogenic alpha-amylase may also be a variant of the maltogenic alpha-amylase from *B. stearothermophilus* as disclosed in, e.g., WO1999/043794; WO2006/032281; or WO2008/148845, e.g., Novamyl® 3D.

An anti-staling amylase for use in the invention may also be an amylase (glucan 1,4-alpha-maltotetrahydrolase (EC 3.2.1.60)) from *Pseudomonas* saccharophilia or variants thereof, such as any of the amylases disclosed in WO1999/050399, WO2004/111217, or WO2005/003339.

The glucoamylase for use in the present invention include the *A. niger* G1 or G2 glucoamylase (Boel et al. (1984), EMBO J. 3 (5), p. 1097-1102), the *A. awamori* glucoamylase disclosed in WO 84/02921, or the *A. oryzae* glucoamylase (Agric. Biol. Chem. (1991), 55 (4), p. 941-949). A suitable commercial glucoamylase is GoldCrust® obtainable from Novozymes A/S.

The glucose oxidase may be a fungal glucose oxidase, in particular an *Aspergillus niger* glucose oxidase (such as GLUZYME®, available from Novozymes A/S).

The xylanase which may be of microbial origin, e.g., derived from a bacterium or fungus, such as a strain of *Aspergillus*, in particular of *A. aculeatus, A. niger, A. awamori*, or *A. tubigensis*, from a strain of *Trichoderma*, e.g. *T. reesei*, or from a strain of *Humicola*, e.g., *H. insolens*.

Suitable commercially available xylanase preparations for use in the present invention include PANZEA BG, PENTOPAN MONO BG and PENTOPAN 500 BG (available from Novozymes A/S), GRINDAMYL POWERBAKE (available from Danisco), and BAKEZYME BXP 5000 and BAKEZYME BXP 5001 (available from DSM).

The phospholipase may have phospholipase A1, A2, B, C, D or lysophospholipase activity; it may or may not have lipase activity. It may be of animal origin, e.g., from pancreas, snake venom or bee venom, or it may be of microbial origin, e.g., from filamentous fungi, yeast or bacteria, such as *Aspergillus* or *Fusarium*, e.g., *A. niger*, *A. oryzae* or *F. oxysporum*. A preferred lipase/phospholipase from *Fusarium oxysporum* is disclosed in WO 98/26057. Also, the variants described in WO 00/32758 may be used.

Suitable phospholipase compositions are LIPOPAN F and LIPOPAN XTRA (available from Novozymes A/S) or PANAMORE GOLDEN and PANAMORE SPRING (available from DSM).

Enzyme Treatment

The endopeptidase according to the invention is added to the dough ingredients, e.g., indirectly to the dough by adding it to the flour used to prepare the dough, or directly to the dough itself.

The endopeptidase may be added to flour or dough in any suitable form, such as, e.g., in the form of a liquid, in particular a stabilized liquid, or it may be added to flour or dough as a substantially dry powder or granulate.

Granulates may be produced, e.g., as disclosed in U.S. Pat. Nos. 4,106,991 and 4,661,452. Liquid enzyme preparations may, for instance, be stabilized by adding a sugar or sugar alcohol or lactic acid according to established procedures. Other enzyme stabilizers are well-known in the art.

Pre-Mixes

It will often be advantageous to provide the enzyme(s) used in the treatment of the present invention in admixture with other ingredients used to improve the properties of dough products. These are commonly known in the art as "pre-mixes," which usually comprise flour.

Hence, in a further aspect, the present invention relates to a premix for improving the quality of dough used to prepare a flat bread product or flat bread products, which premix comprises endopeptidase and one or more dough ingredients, in particular flour such as flour from grains, such as, wheat flour, corn flour, rye flour, barley flour, oat flour, rice flour, or sorghum flour, and any combinations thereof.

The premix may also comprise one or more enzymes selected from the group consisting of amylase, maltogenic amylase, beta amylase, catalase, cellulytic enzyme, chitinase, cutinase, cyclodextrin glycosyltransferase, deoxyribonuclease, esterase, glucan 1,4-alpha-maltotetrahydrolase, glucanase, galactanase, alpha-galactosidase, beta-galactosidase, glucoamylase, glucose oxidase, alpha-glucosidase, beta-glucosidase, haloperoxidase, hemicellulytic enzyme, invertase, laccase, lipase, mannanase, mannosidase, oxidase, pectinolytic enzymes, peptidoglutaminase, peroxidase, phospholipase, phytase, polyphenoloxidase, proteolytic enzyme, ribonuclease, transglutaminase, and xylanase.

In one embodiment, the pre-mix comprises the endopeptidase according to the invention, a xylanase and/or a phospholipase.

In another embodiment, the present invention relates to a pre-mix comprising the endopeptidase of the present invention and flour, such as, flour from grains, such as, wheat flour, corn flour, rye flour, barley flour, oat flour, rice flour, sorghum flour, and any combinations thereof, and one or more additional enzymes, as previously described.

The pre-mix composition may be in liquid form or dry or substantially dry form.

The invention described and claimed herein is not to be limited in scope by the specific embodiments herein disclosed, since these embodiments are intended as illustrations of several aspects of the invention. Any equivalent embodiments are intended to be within the scope of this invention as well as combinations of one or more of the embodiments.

Various references are cited herein, the disclosures of which are incorporated by reference in their entireties. The present invention is further described by the following examples which should not be construed as limiting the scope of the invention.

EXAMPLES

Example 1

Production of Petit Beurre Biscuits

The following recipe was used:

TABLE 1

| Ingredients | |
|---|---|
| Ingredients | % (w/w) |
| Biscuit flour | 100 |
| Powdered sugar | 20.8 |
| Biscuit margarine | 16.1 |
| Salt | 1 |
| Sodium bi-carbonate | 0.5 |
| Glucose syrup | 1.3 |
| SAPP 10 | 0.5 |
| (Sodium Acid Pyrophosphate) | |
| Ammonium bi-carbonate | 1.1 |
| Water (20° C.) | 26 |

Process:

Powdered sugar, glucose syrup, and biscuit margarine were creamed for 2.30 min in a Kenwood mixer with flat beater.

The SAPP 10 and Sodium bi-carbonate were added to the above mixture, and the mixing was continued at 2 speed till 3 minutes.

Salt and Ammonium bi-carbonate (and SMS in the control/reference) was dissolved with 20° C. water and then added to the above mixture where after mixing was continued at minimum speed till 4 minutes.

Flour plus enzyme according to the invention was added and blended at minimum speed till 5 minutes, scraped, and the mixing was continued till 6 minutes at 1 speed.

Finally, high speed was used for 2.30 minutes.

The dough was rested in a chamber at 40° C./85% RH in covered condition for 15 min.

After resting, the dough was sheeted by forming 8 layers to a final sheet thickness 1.75 mm.

Marking was made on biscuit sheet with Dough Roller Docker and cut with defined weight and baked for 8±1 min at 210-220° C.

Enzyme According to the Invention:

A: Control/reference: 0 mg enzyme. 100 ppm sodium metabisulfite (SMS)

B: 20 mg SEQ ID NO:1 enzyme protein per kg flour. 0 ppm sodium metabisulfite (SMS)

Results:

The sensory test was conducted by 15 people considering appearance, crunchiness, taste, and liking preference.

TABLE 2

| Result of sensory test | | | | | | |
|---|---|---|---|---|---|---|
| Attributes | | | | | A | B |
| Shape | 1 Uneven shape | 5 Reference | 10 Even shape | | 5 | 5 |
| Color | 1 Light | 5 Reference | 10 Dark | | 5 | 6 |
| Surface fingerprints | 1 Low/bad | 5 Reference | 10 High/Good | | 5 | 6 |
| Overall visual quality (including appearance, texture) | 1 Low/bad | 5 Reference | 10 High/Good | | 5 | 5.5 |

TABLE 2-continued

| Result of sensory test | | | | | | |
|---|---|---|---|---|---|---|
| Attributes | | | | | A | B |
| Hardness | 1 Soft | 5 Reference | 10 Hard | | 5 | 4 |
| Crispiness | 1 Less brittle | 5 Reference | 10 Crispy(brittle) | | 5 | 6 |
| Crunchiness | 1 Less crunchy | 5 Reference | 10 More crunchy | | 5 | 6 |
| Melting | 1 Low melting | 5 Reference | 10 High | | 5 | 7 |
| Overall eating quality (including taste, mouthfeel) | 1 Low/bad | 5 Reference | 10 High/good | | 5 | 6.5 |

The result of the sensory testing showed that especially the eating properties were improved by using the enzyme solution according to the present invention compared to using sodium metabisulfite.

The invention claimed is:

1. A method for increasing softness and relaxation of a dough, comprising
    a) adding at least one endopeptidase having at least 60% identity to SEQ ID NO:1 or SEQ ID NO:2 to flour or to a dough comprising a flour, wherein no L-cystein and/or sodium metabisulfite is added to the dough;
    b) kneading the dough; and
    c) making the dough into an edible product;
    wherein the dough has increased softness and relaxation compared to a dough which is prepared under the same conditions but no endopeptidase having at least 60% identity to SEQ ID NO: 1 or SEQ ID NO: 2 is added to the flour or dough comprising a flour.

2. The method according to claim 1, wherein the edible product is selected from the group consisting of bread, flat bread, buns, crackers, pasta, noodles, laminated baking products, biscuits, baguettes, and pizzas.

3. The method according to claim 1, wherein the edible product is biscuits.

4. The method according to claim 1, wherein the flour is selected from the group consisting of wheat flour, corn flour, rye flour, barley flour, oat flour, rice flour, sorghum flour, and a combination thereof.

5. The method according to claim 1, wherein the dough has increased elasticity compared to a dough prepared under the same conditions but wherein no endopeptidase having at least 60% identity to SEQ ID NO: 1 or SEQ ID NO:2 is added to the flour or dough comprising a flour.

6. The method according to claim 1, wherein the at least one endopeptidase is added in an amount of 0.1-1000 mg of enzyme protein per kg of flour.

7. The method according to claim 1, wherein the dough has improved extensibility compared to a dough prepared under the same conditions but wherein no endopeptidase having at least 60% identity to SEQ ID NO: 1 or SEQ ID NO: 2 is added to the flour or dough comprising a flour.

8. The method according to claim 1, wherein the dough further comprises one or more enzymes selected from the group consisting of amylase, maltogenic amylase, beta amylase, aminopeptidase, carboxypeptidase, catalase, cellulytic enzyme, chitinase, cutinase, cyclodextrin glycosyltransferase, deoxyribonuclease, esterase, glucan 1,4-alpha-maltotetrahydrolase, glucanase, galactanase, alpha-galactosidase, beta-galactosidase, glucoamylase, glucose oxidase, alpha-glucosidase, beta-glucosidase, haloperoxidase, hemicellulytic enzyme, invertase, laccase, lipase, mannanase, mannosidase, oxidase, pectinolytic enzymes, peptidoglutaminase, peroxidase, phospholipase, phytase, polyphenoloxidase, proteolytic enzyme, ribonuclease, transglutaminase, and xylanase.

9. The method according to claim 1, wherein the at least one endopeptidase has at least 70% identity to SEQ ID NO: 1 or SEQ ID NO: 2.

10. The method according to claim 1, wherein the at least one endopeptidase has at least 80% identity to SEQ ID NO: 1 or SEQ ID NO: 2.

11. The method according to claim 1, wherein the at least one endopeptidase has at least 90% identity to SEQ ID NO: 1 or SEQ ID NO: 2.

12. The method according to claim 1, wherein the at least one endopeptidase has at least 95% identity to SEQ ID NO: 1 or SEQ ID NO: 2.

13. The method according to claim 1, wherein the at least one endopeptidase is the endopeptidase of SEQ ID NO: 1 or SEQ ID NO: 2.

* * * * *

SEQUENCE LISTING

```
<160> NUMBER OF SEQ ID NOS: 2

<210> SEQ ID NO 1
<211> LENGTH: 188
<212> TYPE: PRT
<213> ORGANISM: Nocardiopsis sp.

<400> SEQUENCE: 1

Ala Asp Ile Ile Gly Gly Leu Ala Tyr Thr Met Gly Gly Arg Cys Ser
1               5                   10                  15

Val Gly Phe Ala Ala Thr Asn Ala Ala Gly Gln Pro Gly Phe Val Thr
            20                  25                  30

Ala Gly His Cys Gly Arg Val Gly Thr Gln Val Thr Ile Gly Asn Gly
        35                  40                  45

Arg Gly Val Phe Glu Gln Ser Val Phe Pro Gly Asn Asp Ala Ala Phe
    50                  55                  60

Val Arg Gly Thr Ser Asn Phe Thr Leu Thr Asn Leu Val Ser Arg Tyr
65                  70                  75                  80

Asn Thr Gly Gly Tyr Ala Thr Val Ala Gly His Asn Gln Ala Pro Ile
                85                  90                  95

Gly Ser Ser Val Cys Arg Ser Gly Ser Thr Thr Gly Trp His Cys Gly
            100                 105                 110

Thr Ile Gln Ala Arg Gly Gln Ser Val Ser Tyr Pro Glu Gly Thr Val
        115                 120                 125

Thr Asn Met Thr Arg Thr Thr Val Cys Ala Glu Pro Gly Asp Ser Gly
    130                 135                 140

Gly Ser Tyr Ile Ser Gly Thr Gln Ala Gln Gly Val Thr Ser Gly Gly
145                 150                 155                 160

Ser Gly Asn Cys Arg Thr Gly Gly Thr Thr Phe Tyr Gln Glu Val Thr
                165                 170                 175

Pro Met Val Asn Ser Trp Gly Val Arg Leu Arg Thr
            180                 185

<210> SEQ ID NO 2
<211> LENGTH: 248
<212> TYPE: PRT
<213> ORGANISM: Fusarium oxysporum
```

```
<400> SEQUENCE: 2

Met Val Lys Phe Ala Ser Val Val Ala Leu Val Ala Pro Leu Ala Ala
1               5                   10                  15

Ala Ala Pro Gln Glu Ile Pro Asn Ile Val Gly Gly Thr Ser Ala Ser
                20                  25                  30

Ala Gly Asp Phe Pro Phe Ile Val Ser Ile Ser Arg Asn Gly Gly Pro
            35                  40                  45

Trp Cys Gly Gly Ser Leu Leu Asn Ala Asn Thr Val Leu Thr Ala Ala
        50                  55                  60

His Cys Val Ser Gly Tyr Ala Gln Ser Gly Phe Gln Ile Arg Ala Gly
65                  70                  75                  80

Ser Leu Ser Arg Thr Ser Gly Gly Ile Thr Ser Ser Leu Ser Ser Val
                85                  90                  95

Arg Val His Pro Ser Tyr Ser Gly Asn Asn Asn Asp Leu Ala Ile Leu
                100                 105                 110

Lys Leu Ser Thr Ser Ile Pro Ser Gly Gly Asn Ile Gly Tyr Ala Arg
                115                 120                 125

Leu Ala Ala Ser Gly Ser Asp Pro Val Ala Gly Ser Ser Ala Thr Val
    130                 135                 140

Ala Gly Trp Gly Ala Thr Ser Glu Gly Gly Ser Ser Thr Pro Val Asn
145                 150                 155                 160

Leu Leu Lys Val Thr Val Pro Ile Val Ser Arg Ala Thr Cys Arg Ala
                165                 170                 175

Gln Tyr Gly Thr Ser Ala Ile Thr Asn Gln Met Phe Cys Ala Gly Val
                180                 185                 190

Ser Ser Gly Gly Lys Asp Ser Cys Gln Gly Asp Ser Gly Gly Pro Ile
        195                 200                 205

Val Asp Ser Ser Asn Thr Leu Ile Gly Ala Val Ser Trp Gly Asn Gly
        210                 215                 220

Cys Ala Arg Pro Asn Tyr Ser Gly Val Tyr Ala Ser Val Gly Ala Leu
225                 230                 235                 240

Arg Ser Phe Ile Asp Thr Tyr Ala
                245
```